US009310355B1

(12) United States Patent
Nagai et al.

(10) Patent No.: US 9,310,355 B1
(45) Date of Patent: Apr. 12, 2016

(54) METHODOLOGY OF DENTAL CARIES DETECTION

(71) Applicant: President and Fellows of Harvard College, Cambridge, MA (US)

(72) Inventors: Shigemi Nagai, Lexington, MA (US); Masazumi Nagai, Lexington, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 14/743,501

(22) Filed: Jun. 18, 2015

Related U.S. Application Data

(60) Provisional application No. 62/180,373, filed on Jun. 16, 2015.

(51) Int. Cl.
*A61K 6/00* (2006.01)
*A61B 5/00* (2006.01)
(Continued)

(52) U.S. Cl.
CPC .............. *G01N 33/52* (2013.01); *A61B 5/4547* (2013.01); *A61C 19/063* (2013.01); *A61K 8/24* (2013.01); *A61Q 11/00* (2013.01); *B65D 81/32* (2013.01); *C01B 25/375* (2013.01); *A61B 5/0088* (2013.01); *A61C 5/04* (2013.01); *A61C 5/062* (2013.01); *A61C 9/0006* (2013.01); *A61C 17/00* (2013.01); *A61K 6/083* (2013.01); *A61K 6/087* (2013.01); *A61K 6/10* (2013.01); *A61K 8/18* (2013.01); *A61K 8/22* (2013.01); *A61K 8/466* (2013.01); *A61K 8/8176* (2013.01); *A61K 8/891* (2013.01); *A61K 49/006* (2013.01); *A61K 2800/43* (2013.01); *A61K 2800/434* (2013.01); *A61K 2800/58* (2013.01); *A61K 2800/88* (2013.01); *A63B 71/085* (2013.01); *G01N 2800/18* (2013.01)

(58) Field of Classification Search
CPC ......... A61K 6/10; A61K 6/083; A61K 6/087; A61K 8/466; A61K 2800/43; A61K 2800/434; A61K 49/006; A61K 8/18; A61K 8/22; A61K 8/8176; A61K 8/891; A61B 5/4547; A61C 9/0006; A61C 19/063
See application file for complete search history.

(56) References Cited

U.S. PATENT DOCUMENTS 2,703,452 A    3/1955  Getz
3,309,274 A    3/1967  Brillilant
(Continued)

OTHER PUBLICATIONS

Gupta et al., "Dialysate iron therapy: Infusion of soluble ferric pyrophosphate via the dialysate during hemodialysis", Kidney International, vol. 55 (1999), pp. 1891-1898.
(Continued)

*Primary Examiner* — Lyle Alexander
*Assistant Examiner* — Jennifer Wecker
(74) *Attorney, Agent, or Firm* — Lerner, David, Littenberg, Krumholz & Mentlik, LLP

(57) ABSTRACT

Disclosed are methods for detecting demineralization of a surface of a tooth, comprising a) contacting the tooth of a subject with an orally acceptable, binding composition comprising a binding agent that binds to a demineralized surface of the tooth; b) removing unbound binding compound; c) contacting the tooth with an orally acceptable, detector composition comprising a probe compound that reacts with the binding agent to form a visually detectable reaction product; and d) detecting formation of the reaction product as an indication of the presence or extent of surface demineralization of the tooth. Systems, kits, and compositions for practicing the methods are also provided.

28 Claims, 7 Drawing Sheets

(51) Int. Cl.

| | |
|---|---|
| *A61C 9/00* | (2006.01) |
| *G01N 33/52* | (2006.01) |
| *A61Q 11/00* | (2006.01) |
| *A61K 8/24* | (2006.01) |
| *C01B 25/37* | (2006.01) |
| *B65D 81/32* | (2006.01) |
| *A61C 19/06* | (2006.01) |
| *A61K 6/10* | (2006.01) |
| *A61C 5/04* | (2006.01) |
| *A61C 17/00* | (2006.01) |
| *A61K 6/083* | (2006.01) |
| *A61K 8/81* | (2006.01) |
| *A61K 8/46* | (2006.01) |
| *A61K 49/00* | (2006.01) |
| *A61K 6/087* | (2006.01) |
| *A63B 71/08* | (2006.01) |
| *A61C 5/06* | (2006.01) |
| *A61K 8/891* | (2006.01) |
| *A61K 8/18* | (2006.01) |
| *A61K 8/22* | (2006.01) |

(56) References Cited

U.S. PATENT DOCUMENTS

| | | | |
|---|---|---|---|
| 3,339,547 A | 9/1967 | Drabkowski | |
| 3,536,069 A | 10/1970 | Gores | |
| 3,654,703 A | 4/1972 | McAdoo | |
| 4,347,233 A | 8/1982 | Yamauchi et al. | |
| 5,415,544 A | 5/1995 | Oxman et al. | |
| 6,749,428 B2 | 6/2004 | DiMarino et al. | |
| 8,394,052 B2 | 3/2013 | Jessop et al. | |
| 8,485,821 B2 | 7/2013 | Prencipe et al. | |
| 8,647,119 B1 * | 2/2014 | Nagai | A61B 5/0088 433/215 |
| 8,721,332 B2 | 5/2014 | Fischer et al. | |
| 2010/0034750 A1 * | 2/2010 | Perfect | A61K 49/006 424/9.7 |
| 2013/0224270 A1 * | 8/2013 | Robinson | A61K 8/19 424/401 |

OTHER PUBLICATIONS

Zimmerman, Elmer W., "Iron gallate inks—liquid and powder", U.S. Department of Commerce National Bureau of Standards, Research Paper RP807, Part of Journal of Research of the National Bureau of Standards, vol. 15, Jul. 1935.

A. Lussi, Validity of Diagnostic and Treatment Decisions of Fissure Caries, Caries Research, 25(4):296-303 (1991).

George K. Stookey, MSD, PHD, Quantitative Light Fluorescence: A Technology for Early Monitoring of the Caries Process, The Dental Clinics of North America, 49 (2005) 753-770.

John D.B. Featherstone, PHD, Caries Detection and Prevention with Laser Energy, Dental Clinics of North America, 44(4):955-69 (2000).

Schneiderman, et al., Assessment of Dental Caries with Digital Imaging Fiber-Optic TransIllumination (DIFOTI™): In vitro Study, Caries Research, 31:103-10 (1997).

Heinrich-Weltzien, et al., Quantitative light-induced fluorescence (QLF)—A potential method for the dental practitioner, Quintessence Int. 34(3):181-8 (2003).

Shi, et al., Occlusal Caries Detection with KaVo DIAGNOdent and Radiography: An in vitro Comparison, Caries Res. 34:151-8 (2000).

Kuljanin, et al., Spectrophotometric determination of alendronate in pharmaceutical formulations via complex formation with Fe(III) ions, Journal of Pharmaceutical and Biomedical Analysis, 28(6):1215?20 (2002).

Kontturi, et al., Structures of Bisphosphate Metal Complexes: Zinc and Cadmium Complexes of Clodronate and Its Partial Ester Derivatives, Inorganic Chemistry, 44(7):2400-6 (2005).

Guerrieri, et al., Minimal intervention dentistry: part 4. Detection and diagnosis of initial caries lesions, British Dental Journal, 213(11):551-7 (2012).

Theocharopoulou, et al., Use of the ICDAS system and two fluorescence-based intraoral devices for examination of occlusal surfaces, European Journal of Paediatric Dentistry, 16(1):51-5 (2015).

Van Hilsen and Jones, Compairing potential early caries assessment methods for teledentistry, BIOMED Central Oral Health, 13:16 (2013).

Susan Higham, Caries Process and Prevention Strategies: Demineralization/Remineralization, Crest® + Oral-B® at dentalcare.com (Continuinig Education Course, Revised Aug. 28, 2014).

Gumienna-Kontecka, et al., Bisphosphonate chelating agents: complexation of Fe(III) and Al(III) by 1-phenyl-1-hydroxymethylene bisphosphonate and its analogues, Inorganica Chimica Acta. 2002; 339:111-118. DOI: 10.1016/S0020-1693(02)00918-0.

Kamburoglu K, Kolsuz E, Murat S Yüksel S, Ozen T., Proximal caries detection accuracy using intraoral bitewing radiography, extraoral bitewing radiography and panoramic radiography, Dentomaxillofac Radiology Sep. 2012;41 (6):450-9.

Rainey JT, Air abrasion: an emerging standard of care in conservative operative dentistry. The Dental Clinics of North America, 2002;46(2)185-209.

Nyvad B., Diagnosis versus Detection of Caries. Caries Res. 2004; 38:192-198.

* cited by examiner

Color signal can visualize caries even before caries can be detected in a clinical exam.

Color chart (top) and present invention test tray (bottom)

METHODOLOGY OF DENTAL CARIES DETECTION

CROSS-REFERENCE TO RELATED APPLICATIONS

The present application claims the benefit of the filing date of U.S. Provisional Patent Application No. 62/180,373 filed Jun. 16, 2015, the disclosure of which is hereby incorporated herein by reference.

BACKGROUND OF THE INVENTION

Dental caries is an infectious disease caused by the complex interaction of cariogenic (caries-causing) bacteria with sugars on the tooth surface over time. Cariogenic bacteria metabolize sugars for energy, and produce organic acids as byproducts. The acids lower the pH in the plaque biofilm. Featherstone, Oral Health Prev. Dent. 2(suppl. 1):259-64 (2004). The enamel, which is the hard, outmost layer of teeth, is composed mostly of crystalline hydroxyapatite (HPA). HPA is primarily composed of phosphate ions and calcium ions. Under normal conditions, there is a stable equilibrium between the calcium and phosphate ions in saliva and the crystalline HPA in the tooth enamel. When the pH drops below a critical level (5.5 for enamel, and 6.2 for dentin, which is the hard layer under the enamel), it causes the dissolution of HPA—a process called demineralization. Since enamel is the primary contact with cariogenic bacteria and is also the only tissue of the tooth that does not have the ability to grow or repair itself after maturation, the importance of preventing demineralization in this area becomes magnified. Robinson et al., Eur. J. Oral Sci. 106(Suppl. 1):282-91 (1998).

Demineralization can be reversed. When the pH is elevated by the natural buffer capacity of saliva, mineral gets reincorporated into the tooth. This process is known as remineralization. See, Featherstone, supra.; Fejerskov, Comm. Dent. Oral Epidemiol. 25(1):5-12 (1997); and Silverstone, Aust. Dent. J. 25(3):163-8 (19980). In some instances when the demineralization is limited to a shallow surface, remineralization can halt or even reverse the caries process. Fejerskov et al. (Eds.), *Dental Caries: The Disease and its Clinical Management*, 2nd ed. Oxford, United Kingdom: Blackwell Munksgaard; 2008. Saliva and fluoride are two key players in the remineralization process. Healthy saliva contains large amounts of the calcium and phosphate ions that can replenish lost minerals in the hard tooth structure. Fluoride can be incorporated into the tooth structure to strengthen it. Fejerskov, supra.; Tenovuo, Acta Odontol. Scand. 56:250-6 (1998).

In order to prevent the formation of dental caries, factors in the oral cavity must be highly favorable for mineralization to occur in order to be effective. Otherwise, the remineralization process may have little or no influence or not occur at all, in which case caries will develop. Thus, caries is the results of a series of demineralization/remineralization cycles where, over time, demineralization conditions prevail.

The Center for Disease Control (CDC) has reported that 45 million Americans have very limited access to oral health care due to lack of insurance. Centers for Disease Control and Prevention: National Center for Health Statistics (2014). For pediatric and adult populations, limited coverage and access to oral healthcare have led to many with untreated oral disease. Manski, et al., Dental Use, Expenses, Private Dental Coverage, and Charges, 1996 and 2004; Rockville, Md.: Agency for Healthcare Research and Quality; 2007; Manski, et al., Comm. Dent. Health 24(4):204-12 (2007); and Manski, et al., Am. J. Pub. Health 1014(2):e80-e87 (2014). The CDC reports that 53 million people live with untreated tooth decay in their permanent teeth. Centers for Disease Control and Prevention, Division of Oral Health (U.S.) Oral Health: Preventing Cavities, Gum Disease, and Tooth Loss (Jun. 3, 2009). Thus, dental caries remains a serious chronic disease. Brown, et al. J. Am. Dent. Assoc. 131(2):223-31 (2000). Lower income and socioeconomically underprivileged groups have a much higher prevalence of untreated dental caries.

Undetected caries results in invasive surgical restoration, potentially subjecting the patient to a lifetime of treatment, such as fillings, root canal treatment (RCT) and crowns. Furthermore, poor oral health is detrimental for children since it affects their nutrition, growth and development. Untreated childhood oral diseases can lead to pain, dentofacial anomalies, dental abscess, and destruction of bone. United States Department of Health and Human Services (U.S.D.H.S.) Oral Health in America: A Report of the Surgeon General. National Institute of Health, 2000. Furthermore, trends in US hospital-based emergency department visits involving dental conditions have been studied, results of which have found that out of 215,073 emergency visits with dental conditions in 2008, 50% of the visits were dental caries related. Total oral disease-related emergency department charges across the United States were $14.2 million, followed by total hospitalization charges of $162 million. During the period studied (i.e., 2008-2010), dental care expenditures and hospital resource charges across the entire United States for oral disease were 2.7 billion dollars. Allareddy, et al., J. Am. Dent. Assoc. 145(4):331-7 (2014); Wallace, et al., Am. J. Public Health 101(11):2144-50 (2011).

Even though dental caries is largely preventable, it remains the most common chronic disease among children and adolescents. Healthy oral hygiene and diet behaviors are as important in preventing caries as a major public health milestone such as water fluoridation. Currently, even though the benefits of both brushing and flossing are well established, 92% of university students were found to brush at least twice a day, whereas only 15% flossed their teeth daily. Rimondini, et al., J. Clin. Periodont. 28:2007-11 (2001). While brushing teeth daily is relatively well accepted, only few adhere to the recommended daily flossing regimen.

In vitro studies have demonstrated that diagnosis with the dental professional is correct in fewer than 50% of cases. Lussi, Caries Res. 25(4):296-303 (1991). This has been found to be especially true in the case of incipient caries and occlusal caries. Stookey, Dent. Clin. North Am. 49(4):753-70 (2005). It has also been shown that although bitewing radiographs (i.e., X-rays) show high sensitivity (0.69-0.84) and specificity (0.94-0.99) in diagnosing interproximal caries, they are ineffective in detecting occlusal caries. Camburoglu, et al. Dentomaxillofac. Radiol. 41(6):450-9 (2012); Featherstone, Dent. Clin. North Am. 44(4):955-69 (2000). Furthermore, X-ray images usually significantly underestimate the actual size or depth of a carious lesion. White, et al., Oral Radiology: Principles and Interpretation (2003), 5th ed. (Mosby). By the time a lesion is visible on an X-ray bitewing, the only effective therapy is invasive surgical restoration, which potentially subjects the patient to a lifetime of expensive treatment.

Currently, there are a number of commercially available optical methods for caries detection, including, for example, digital imaging under transillumination (Schneiderman, et al., Caries Res. 31:103-10 (1997)), quantitative light-induced fluorescence (Heinrich-Weltzien, et al., Quintessence Int. 34(3):181-8 (2003)), and laser fluorescence (Shi, et al. Caries Res. 34:151-8 (2000). However, not even these diagnostic tools have proven to be effective in accurately detecting early caries.

The World Oral Health Report published in 2003 by the World Health Organization ("the WHO"), indicates that dental caries is a major health problem in most industrialized countries, affecting 60-90% of school children and most adults. Petersen, *The World Oral Health Report* 2003: *Continuous Improvement of Oral Health in the* 21*st Century—The Approach of the WHO Global Health Programme* (World Health Organization, Geneva, 2003). Furthermore, a review of the available epidemiological data from many countries indicates that there is a significant increase in the prevalence of caries and have described it as a "pending public health crisis." Bagramian et al., Am. J. Dent. 22(1):3-8 (2009); Sudha et al., J. Indian Soc. Pedod. Prev. Dent. 23(2):74-9 (2005). Thus, a need remains for sensitive and accurate diagnostic methods for detection of demineralization and early caries detection in teeth, and which can be more conveniently carried out by lay persons themselves, before consulting with dental professionals.

BRIEF SUMMARY OF THE INVENTION

The present invention exploits the use of two different kinds of chemical agents, which are orally acceptable and may even be of food-grade quality. One agent, referred to herein as a binding agent or compound, binds to demineralized surfaces on teeth. The binding is believed to be selective in that the binding agent binds to demineralized surfaces on a tooth but not to non-demineralized surfaces. The other agent, referred to herein as a probe compound, undergoes a reaction with the binding agent and produces a reaction product or complex that because of its color that can be seen with the naked eye. The intensity of the color produced by the reaction is proportional to the extent of demineralization, and thus may be indicative of caries formation.

Accordingly, a first aspect of the present invention is directed to a method for detecting demineralization of a surface of a tooth, comprising a) contacting the tooth (e.g., by introducing into the oral cavity) of a subject with an orally acceptable binding composition comprising a binding agent or compound that binds to a demineralized surface of the tooth; b) removing unbound binding agent; c) contacting the tooth with an orally acceptable detector composition comprising a probe compound that reacts with the binding agent to form a visually detectable reaction product; and d) detecting formation of the reaction product as an indication of the presence or extent of surface demineralization of the tooth.

A second aspect of the present invention is directed to a kit for detecting demineralization of a surface of a tooth, comprising a) a first container comprising an orally acceptable, binding composition comprising a binding agent or compound, wherein the binding agent binds to a demineralized surface of the tooth; and b) a second container comprising an orally acceptable, detector composition comprising a probe compound that reacts with the binding agent to form a visually detectable reaction product.

A third aspect of the present invention is directed to a system for detecting demineralization of a surface of a tooth, comprising a) an orally acceptable, binding composition comprising a binding agent or compound that binds to a demineralized surface of the tooth; and b) an orally acceptable, detector composition comprising a probe compound that reacts with the binding agent to form a visually detectable reaction product.

A fourth aspect of the present invention is directed to the orally acceptable binding compositions, per se. The composition may be in the form of a paste, varnish, dentifrice, gel, cream, gum, candy, mint, spray, mouthwash, whitening system, powder, rinse, or foam. In some embodiments, the composition is non-ingestible, i.e., not formulated or intended for ingestion or consumption.

Yet a fifth aspect of the present invention is directed to the orally acceptable detector compositions per se, which contain the probe compound. In some embodiments, the probe compound is a polyphenol or a porphyrin which can react with the transition metal coordination complex and form a visually detectable reaction product. In some embodiments, the composition is non-ingestible. In some embodiments, the composition further includes an active dental agent.

A sixth aspect of the present invention is directed to a method for remineralizing a demineralized surface of a tooth, comprising a) detecting a demineralized surface of a tooth by i) contacting the tooth of a subject with an orally acceptable, binding composition comprising a binding agent or compound, whereby the binding agent binds to a demineralized surface of the tooth; ii) removing unbound binding agent; iii) contacting the tooth with an orally acceptable, detector composition comprising a probe compound, whereby the probe compound reacts with the binding agent to form a visually detectable reaction product; and iv) detecting formation of the reaction product between the binding agent and the probe compound as an indication of the presence or extent of surface demineralization of the tooth; and b) applying an orally acceptable composition comprising a remineralizing agent to the tooth.

With respect to any one or more of the aspects of the present invention, in some embodiments the binding agent is an orally acceptable transition metal coordination complex. In some embodiments, the transition metal that forms the transition metal coordination complex includes Fe, Cu, Co, Pt, Sn, Ag, Mn, Ti, and Zn. In some embodiments, the transition metal (including specific valence) includes Fe (III), Cu (II), Co (III), Pt (IV), Sn (IV), Ag (I), Mn (IV), Ti (IV), and Zn (II). In some embodiments of the present invention, the binding composition is a dentifrice (e.g., a toothpaste), that contains a Fe metal coordination complex, e.g., Fe (III)-pyrophosphate, and the detector composition is a dental impression material that includes flour, a gum and a hydrophilic clay. In some embodiments, the probe compound is a polyphenol, e.g., gallic acid or an ester thereof such as propyl gallate.

The present invention provides numerous advantages compared to current detection, systems, and methodologies employed by dental professionals. First and foremost, the present invention may be purchased as an "over-the-counter" product which is inexpensive and disposable after use. Thus, it may be used by individuals, without having to resort to a dental professional. However, the invention is not limited to "home" use and may indeed be used by dental professionals, in which case aspects of the present invention such as the kits may contain fewer elements (as described hereinbelow). The invention allows for a relatively simple and fast visual detection of demineralization in both reversible and irreversible stages, and which may be viewed 3-dimensionally rather than the 2-dimensional view provided by X-rays. The compositions that are utilized in the practice of the present invention, e.g., a binding composition and a detector composition, include ingredients that are all orally acceptable, and in some embodiments, of food-grade quality. The present invention also enhances self-compliance with respect to good oral hygiene. By providing a cost-effective, easily accessible, safe and non-radiographic means for early detection of demineralization, and that allows the user to easily visualize and interpret test results, and to even track results over time, the individual may be in a position to self-monitor his or her dental health and affirmatively exercise preemptive care and reverse the demineralization process or seek dental care and receive adequate professional treatment so as to prevent further demineralization.

Significantly, the present invention also offers advantages in terms of accuracy. The data contained herein demonstrate that the present invention is more accurate in diagnosing or detecting caries formation than several detection systems and methodologies in clinical use. Significantly, the data show that the present invention reduces the number of both false-positive results and positive-negative results.

Since aspects of the present invention provide veritable screening tools that can be used by lay persons and non-dental professionals, it may have wide public health implications. For instance, it has been demonstrated that across all ages, 35% of the U.S. population, or about 108 million people per year, visit a physician but not a dentist. Vujicic, JADA 145 (4):381-2 (2014). Essentially, primary care physicians, registered nurses, and other public health field personnel may utilize the present invention to screen for oral health as a part of routine physical exams. Furthermore, by working in collaboration with large global public health organizations such as oral health foundations, state dental associations, ministries of health, the WHO, and numerous other health related organizations, the present invention may be exploited to promote oral health in many populations through routine screening.

DETAILED DESCRIPTION

The Compositions

The compositions of the present invention are "orally acceptable," which as used herein means that in the ordinary course of usage, they are not intentionally swallowed for purposes of systemic administration but rather are retained in the oral cavity for a time sufficient to contact teeth for the intended purpose and are safe and effective for the intended purpose. In some embodiments, one, some or all of the ingredients used in the compositions may be of "food-grade" quality, which as used herein, refers to an ingredient that is ingestible by, and non-toxic, to humans. A food-grade ingredient, as used in the present invention, does not necessarily impart palatability or nutrition to a food product. Thus, Applicants' usage of the term "food-grade" is believed to be substantially consistent with the criteria described in Chapter 21 of the *Code of Federal Regulations*, promulgated by the U.S. Food and Drug Administration. Unless otherwise indicated, amounts of ingredients are expressed in terms of "% w/v," which means grams of the ingredient per 100 ml of the composition in which it is contained.

Figure 1:
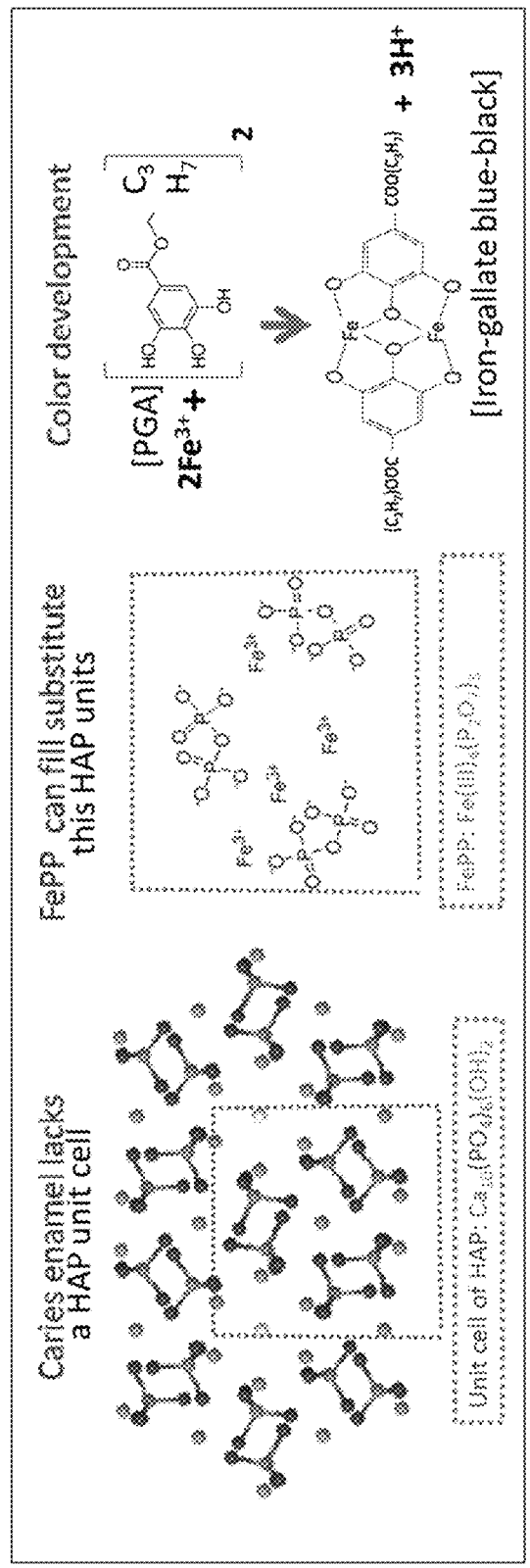
FIG. 1 is a set of schematic diagrams showing a caries enamel lacking a unit cell of HPA, an Fe (III)-type binding agent filling the cell, and the reaction between the binding agent and propyl gallate, which produces iron gallate (which is blueish-black in color).

Binding compositions of the present invention contain an agent or a compound, that binds to a demineralized surface on a tooth. FIG. 1 schematically illustrates the binding of the binding agent to the demineralized surface on a tooth. Without intending to be bound by any particular theory of operation, the binding of the binding agent to a demineralized surface on a tooth is believed to be selective in that the binding agent does not bind to healthy, intact (i.e., non-demineralized) surfaces of teeth, and that the binding agent also stably and selectively binds to demineralized surfaces of teeth, which is not dependent on pH. Any adherence to non-demineralized surfaces is deminimus (i.e., functionally negligible) and due to lesser affinity of the binding compound for the non-demineralized surfaces, is easily washed away such as by rinsing prior to application of the detector composition. The binding of the transition metal coordination complex to a demineralized surface thus enables an accurate detection or diagnosis of demineralization, e.g., caries formation.

In some embodiments, the binding agent or binding compound may be a transition metal coordination complex between the transition metal and a ligand. The IUPAC definition defines a transition metal as an element whose atom has a partially filled d sub-shell, or which can give rise to cations with an incomplete d sub-shell; a consensus is that a transition metal includes any element in the d-block of the periodic table, which includes groups 3 to 12 thereof, and would thus include elements with atomic numbers between 21-30, 39-48, 72-80, and 104-112, and any of the multiple valence states thereof. For purposes of the present invention, zinc is considered to be embraced by the term "transition metal."

Representative examples of transition metals that may form the transition metal coordination complex that may be suitable for use in the present invention include Fe, Cu, Co, Pt, Sn, Ag, Mn, Ti, and Zn. More specific examples of transition metals (including specific valences) that may be suitable for use in the present invention include Fe (III), Cu (II), Co (III), Pt (IV), Sn (IV), Ag (I), Mn (IV), Ti (IV), and Zn (II).

Representative examples of ligands that may be used to form the metal complexes include pyrophosphates (also referred to herein as "PP"), bisphosphonates, peptides, and citrates (e.g., ammonium citrate). Thus, in some embodiments, the transition metal coordination complex is a pyrophosphate transition metal coordination complex, e.g., Fe (III)-pyrophosphate, Co (III)-pyrophosphate, Cu (II)-pyrophosphate, Sn (IV)-pyrophosphate, Pt (IV)-pyrophosphate, Ag (I)-pyrophosphate, Mn (IV)-pyrophosphate, Ti (IV)-pyrophosphate and Zn (II)-pyrophosphate. In some embodiments, the transition metal coordination complex is Fe (III)-pyrophosphate.

In some embodiments, the ligand is a bisphosphonate. Representative examples of such transition metal complexes include alendronate Fe (III), and alendronate Zn (II). See, e.g., Gumienna-Kontecka, Inorganica Chimica Acta 339:111-8 (2002); Kuljanin et al., J. Pharm. Biomed. Anal. 28(6):1215-20 (2002); and Kontturi et al., Inorg. Chem. 44(7):2400-6 (2005).

In some embodiments, the ligand is a peptide. A representative example of such a transition metal complex is Ferrichrome.

In some embodiments, the ligand is a citrate. Representative examples of such transition metal complexes include Fe (III)-ammonium citrate, Cu (II)-ammonium citrate, Zn (II)-ammonium citrate, and Sn (IV)-ammonium citrate.

In other embodiments, the ligand is porphyrin or chlorin. Representative examples of such transition metal coordination complexes that may be useful as the binding agent or compound include Fe (III) chlorin, Cu (II) chlorin, Zn (II) chlorin, and Sn (IV) chlorin.

For ease of administration to the surface of the tooth, the binding agent or compound may be formulated with one or more other ingredients (which may be collectively referred to herein as a "carrier"). In some embodiments, the carrier may be, in and of itself, an oral care composition, representative examples of which include dentifrices (which include pastes, liquids and gels), rinses such as mouthwashes, and whitening systems (including gels). These binding compositions may thus be formulated so as to allow contact with the teeth in any dentally acceptable manner, e.g., pastes, varnishes, creams, candies such as gums and mints, liquids (including aerosol and non-aerosol sprays and syringeable liquids), powders, rinses, and foams. The binding compositions may be formulated as a tablet or capsule. In some embodiments, the carrier composition is a dentifrice such as a toothpaste composition (which under conditions of normal use, involves about 0.2 g to about 1.5 g of toothpaste), or a rinse such as a mouthwash.

The amount of binding agent is effective to bind to a demineralized surface and be detected. The amount will vary depending on numerous factors such as the binding agent, the carrier and the solubility of the agent in the carrier, and that the optimal amount can be determined by persons skilled in the art by using standard techniques in the art. The amount of the binding agent or compound that is to be applied to a tooth or the teeth typically ranges from about 5 mg to about 400 mg, and in some embodiments from about 5 mg to about 50 mg, and in some embodiments (e.g., wherein the binding agent is Fe (III)-PP and the carrier is a toothpaste) from about 1 mg to about 74.5 mg, and in some other embodiments, from about 5 mg to about 50 mg, e.g., about 20 mg, per administration. Expressed in terms of % w/v (e.g., wherein the binding composition is a toothpaste or rinse), the amount of the binding agent (on a dry weight basis) may generally range from about 0.075% w/v to about 7.5% w/v, and in some embodiments from about 1% w/v to about 4% w/v.

The Detector Composition

The detector composition contains a probe compound which undergoes a colorimetric reaction with the binding agent or compound (that adheres to demineralized surfaces on tooth) and forms a visually detectable reaction product. In some embodiments, the probe compound is a polyphenol. Representative examples of polyphenols that may be suitable for use in the present invention include gallic acid, or an ester thereof, e.g., propyl gallate, ethyl gallate, octyl gallate, dodecyl gallate, and epigallocatechin gallate. Other representative examples of polyphenols include resveratrol, quercetin, and rutin. In some embodiments, the probe compound is propyl gallate, which is a food additive that has been approved by the FDA.

In some embodiments, the probe compound is porphyrin or a derivative thereof, representative examples of which include porphine, tetra(4-N-methylpyridyl)porphine, tetraphenylporphine sulfonate, and haematoporphyrin.

The amount of the probe compound contained in the detector composition is sufficient to produce the colorimetric reaction. The probe compound may be present in an amount of about 0.5% w/v to about 10% w/v, and in some embodiments from about 1% w/v to about 5% w/v, and in some other embodiments, from about 2% w/v to about 3% w/v (e.g., about 2.5% w/v).

To facilitate applying the probe compound to the teeth (after application of the binding composition), it may be formulated with an orally acceptable carrier that can be applied to the teeth in accordance with dentally acceptable methods. For example, the probe compound may be formulated in the very same types of oral care compositions as described herein above with respect to the binding agent. In some embodiments, the carrier is semi-solid, pasty or colloidal in nature such that it can form an impression of the teeth when applied thereto (e.g., such as by way of a dental tray, tape, or sheet). Such materials are well known in the art and include, for example, dental impression materials and bite registration materials. These materials do not have to be cured in order to be used in connection with the present invention. Thus, they may be cured or non-cured. Representative dental impression materials that may be suitable for use in the present invention are commercially available from 3M under the tradenames VPS, IMPRINT 3 and 4 VPS, IMPREGUM PENTA Soft, PENTAMIX 3, PENTAMIX Lite, EXPRESS VPS, PERMADYNE, ESPE, ESPE VPS, and PARADIGM VPS. Representative dental impression materials that may be suitable for use in the present invention are commercially available from various manufacturers under the tradenames BLU-MOUSSE VPS, PATTERSON, REGISIL 2x, GENIE, EXBITE II, IMPRINT 4, FUTAR D50-S, ESPE, CORRECT QUICK BITE, R-SI-LINE, MEMOREG, JET BLUE, Occlufast Rock, Jet Bite, Ultradent Clone Bite, and Colorbite Rock.

Representative examples of types of substances that may be used as a carrier particularly in the context of making an impression of a tooth include, for example, polyvinylsiloxanes (PVS), e.g., Ultradent Chromaclone PVS, silicones, natural gum bases (e.g., acacia and chicle), synthetic gum bases (e.g., butyl rubber, butadiene rubber, and polyisobutylene), flours, gelatins, alginates and salts thereof (e.g., sodium alginate and sodium calcium alginate) and Ultradent Chromaclome 5-day stability alginate, clays (e.g., bleaching earths such as sodium bentonite and montmorillonite), waxes, starches (e.g., corn starch), cotton, fibers (e.g., bamboo fiber, hemp fiber, and microfiber), sodium polyacrylate, rubbers (e.g., silicone rubber and polyether rubber), nata de coco, agar, rice, rice cake, and fish cake.

In some embodiments, the detector composition may include at least one ingredient that may be of a food grade quality such as flour. Representative examples of flour that may be suitable for use in the present invention include wheat flour, barley malt flour, brown rice flour, corn flour, ground wheat flour, and soy flour. The amount of flour that may be present in the detector composition generally ranges from about 40% w/v to about 70% w/v, and in some embodiments, from about 45% w/v to about 65% w/v, based on the total volume of the detector composition, and in some other embodiments about 50% w/v to about 60% w/v, e.g., about 55% w/v.

In these embodiments, the detector composition may further include a polymer and/or a viscosity modifier such as agar, alginate, carrageenan, carboxymethylcellulose, gelatin, curdlan, gellan, beta-glucan, or a gum, and which may be used to make an impression of teeth. The polymer may function for purposes of texture, mouthfeel and its ability to mold to teeth to make an impression thereof. Representative examples of such gums include gum tragacanth, guar gum, locust bean gum, xanthan gum, gum karaya and gum Arabic (also known as acacia gum). The polymer, e.g., gum, may be present in the detector composition in an amount that generally ranges from about 15% w/v to about 40% w/v, and in some embodiments from about 20% w/v to about 35% w/v, and in some embodiments from about 25% w/v to about 35% w/v, e.g., about 30% w/v.

In some embodiments, the carrier includes a viscosity modifier to adjust viscosity of the detector composition to the desired level. Examples of viscosity modifiers include hydrophilic polymers such as hydrophilic clays. The term "hydrophilic clay" is generally understood to refer to a clay that is capable of swelling in water and upon hydration, forming a colloidal dispersion. Representative examples of hydrophilic clays that may be useful in the practice of the present invention include silicates containing a cation that may be chosen from calcium, magnesium, aluminium, sodium, potassium and lithium cations, and mixtures thereof, e.g., clays of the smectite family such as montmorillonites, hectorites, bentonites, beidellites and saponites, and also of the family of vermiculites, stevensite and chlorites. The hydrophilic clays may be of natural or synthetic origin. Other examples of hydrophilic clays include synthetic hectorites (also known as laponites), for instance the products sold by the company Laporte under the names Laponite XLG, Laponite RD and Laponite RDS (these products are sodium magnesium silicates and in particular sodium lithium magnesium silicates); bentonites, for instance the product sold under the name Bentone HC by the company Rheox; magnesium aluminium silicates, especially hydrated, for instance the products sold by the Vanderbilt Company under the names Veegum Ultra, Veegum HS and Veegum DGT, or calcium silicates, and especially the product in synthetic form sold by the company under the name Micro-cel C. A particularly suitable clay is sodium bentonite.

The clay may be present in the detector composition in an amount that generally ranges from about 1% w/v to about 10% w/v, and in some embodiments from about 2% w/v to about 4% w/v, and in other embodiments about 2.5% w/v to about 3.5% w/v, e.g., about 3% w/v.

In some other embodiments, the carrier for the probe compound is formulated as a non-paste for application to the teeth via an aerosol or non-aerosol spray, via syringe or as a varnish.

The detector composition may further include an orally acceptable oil, which may also provide viscosity-modifying properties, as well as to reduce stickiness. Representative examples of orally acceptable oils include mineral oil, silicone oil, naphthenic oil, paraffinic oil, and edible oils such as canola oil. The oil may be present in an amount that generally ranges from about 0.25% w/v to about 2.5% w/v and in some embodiments from about 0.5% w/v to about 2% w/v, e.g., 0.75% w/v to about 1% w/v.

The detector composition may also include a humectant, which may prevent hardening of the composition upon exposure to air and impart desirable sweetness of flavor to the composition. Examples of humectants that may be suitable for use in the invention include glycerin, xylitol, sorbitol, polyethylene glycol, and other edible polyhydric alcohols.

In some embodiments, the detector composition may include an enhancing agent, which for purposes of the present invention refers to an agent that facilitates the dissociation of the binding agent from demineralized surfaces on teeth. Representative examples of enhancing agents include chelating agents (e.g., ethylene diaminetetra acetic acid (EDTA) and ethylene bis(oxyethylene nitralo) tetra acetic acid (EGTA)), and fluoride salts (e.g., sodium fluoride and stannic fluoride). The enhancing agent may be present in an amount that generally ranges from about 0.05% w/v to about 2% w/v, and in some embodiments from about 0.1% w/v to about 0.5% w/v, e.g., about 0.25% w/v.

The detector composition may or may not contain water. If water is present, the amount generally varies from about greater than 0 (e.g., about 1, 2, 3, 4, 5, 6, 7, 8, 9, 10%) to about 20% w/v or to about 30% w/v or to about 40% w/v, and in some embodiments from about 25% w/v to about 35% w/v (e.g., about 30% w/v), based on the total volume of the detector composition.

In some embodiments, the detector composition may contain a water-miscible solvent, e.g., lower alkyl glycols e.g., propylene glycol, butylene glycol, glycerin, to aid in the solubilization of the probe compound. The water-miscible solvent may be present in an amount of about 5% w/v to about 10% w/v, and in some embodiments, about 7% w/v to about 9% w/v, e.g., about 8% w/v.

In some embodiments, the binding composition, the detector composition, or both of these compositions may include an active dental agent, representative examples of which include whitening agents, desensitizing agents, and fluorides. Representative examples of whitening agents include peroxy compounds (e.g., hydrogen peroxide, peroxides of alkali and alkaline earth metals, organic peroxy compounds and peroxy acids and salts thereof), chlorine dioxide, chlorites and hypochlorites (e.g., chlorites and hypochlorites of alkali and alkaline earth metals such as lithium, potassium, sodium, magnesium, calcium and barium), and carbamides. Representative examples of desensitizing agents include potassium salts such as potassium citrate, potassium tartrate, potassium chloride, potassium sulfate and potassium nitrate, sodium nitrate, and local or systemic analgesics such as aspirin, codeine, acetaminophen, sodium salicylate and triethanolamine salicylate. Representative examples of fluorides include sodium fluoride, potassium fluoride, stannous fluoride and ammonium fluoride.

In some embodiments, the binding composition, the detector composition, or both of these compositions may contain at least one orally acceptable excipient (e.g., non-active ingredient), representative examples of which include flavoring agents, texturing agents, coloring agents (e.g., dyes), sweeteners, sensate ingredients, and buffering agents/buffers. Flavoring agents are typically chosen from synthetic flavoring liquid and/or oils derived from plants leaves, flowers, and fruits. Representative flavoring liquids include vanillin, sage, marjoram, parsley oil, spearmint oil, cinnamon oil, oil of wintergreen (methylsalicylate), peppermint oils clove oil, bay oil, anise oil, and eucalyptus oil. Other examples include artificial, natural or synthetic fruit flavors such as citrus oil including lemon, orange, banana, grape, lime, apricot and grapefruit and fruit essences including apple, strawberry, cherry, orange, and pineapple; bean and nut derived flavors such as coffee, cocoa, cola, peanut and almond.

Representative examples of sweeteners that may be suitable for use in the present invention include natural and artificial, water soluble, water insoluble and intense sweeteners. The sweetening agent may be dextrose, sucrose, maltose, dextrin, dried invert sugar, mannose, xylose, ribose, glucose, fructose, levulose, galactose, corn syrup, high fructose corn syrup, corn syrup solids, partially hydrolyzed starch, aspartame, saccharin, sugar alcohols such as sorbitol, mannitol, xylitol, maltitol, isomalt, and hydrogenated starch hydrolysate or combinations thereof. Natural or artificial intense sweeteners such as dipeptide based intense sweeteners, monellin, *thaumaoccous danielli*, and L-aspartyl L-phenylalanine methyl ester and soluble saccharin salts may also be useful.

Representative examples of ingredients that provide a sensate benefit (e.g., warming and cooling agents) include menthol, menthyl lactate, wintergreen oil, peppermint oil, spearmint oil, leaf alcohol, camphor, clove bud oil, eucalyptus oil, anethole, methyl salicylate, eucalyptol, cassia, 1-8 menthyl acetate, eugenol, oxanone, alpha-irisone, propenyl guaethol, cinnamon, thymol, linalool, benzaldehyde, and cinnamaldehyde glycerol acetal known as CGA. Examples of coolants include carboxamides, menthol, ketals and diols.

Flavoring agents, sweetening agents and sensate agents are typically used in oral care compositions at levels of from about 0.005% w/v to about 5% w/v.

In some embodiments, the binding composition, the detector composition, or both of these compositions may include a buffering agent or a buffer, e.g., to adjust the pH of the composition to a desired level, e.g., a range of about pH 3 to about pH 10, typically about 5 to about 9, and more typically about 6.5 to about 8 and most typically about 7 to about 8. Representative examples of types of buffering agents that may be suitable for use in the present invention include alkali metal hydroxides, carbonates, sesquicarbonates, borates, citrates, silicates, phosphates, and imidazoles. Examples of specific buffering agents include monosodium phosphate, trisodium phosphate, sodium hydroxide, potassium hydroxide, alkali metal carbonate salts, sodium carbonate, imidazole, pyrophosphate salts, citric acid, potassium citrate, and sodium citrate.

In some embodiments, the binding composition is a dentifrice (e.g., a gel, toothpaste or liquid) that contains 0.075% w/v to about 7.5% w/v Fe (III)-pyrophosphate, and the detector composition contains about 2-3% w/v propyl gallate as the probe compound, about 50-60% w/v flour, about 25-35% w/v gum, about 2-4% w/v clay, about 0.5-2% w/v oil, about 0.1-0.5% w/v enhancing agent, about 25-35% w/v water, and about 7-9% w/v water-miscible solvent.

Methods

To practice the method for detecting demineralization of a surface of a tooth in accordance with the present invention, the tooth or teeth are contacted with the binding agent or compound. As described hereinabove, this step is advantageously practiced simply by brushing the teeth with a dentifrice, e.g., toothpaste, gel or liquid, that contains an effective amount of the binding agent or compound. Typically, the teeth may be brushed for the normal and dentally recommended amount of time e.g., about 15-180 seconds. In some embodiments, the teeth are cleaned beforehand, i.e., prior to contact with the binding composition. Cleaning may involve brushing with a dentifrice, rinsing with mouthwash and/or flossing.

More broadly, and as described herein, the binding composition may be applied to the teeth in accordance with any dentally acceptable manner, and which aside from being applied to teeth via an oral care compositions, may entail application via spray, syringe, or dental appliance such as a tray, strip, or occlusal tape or sheet.

Following the step of contacting the tooth or teeth with the binding composition, unbound binding compound is removed from the teeth or oral cavity. This step is most conveniently conducted by rinsing. In some embodiments this is done simply with water, in order to remove any excess binding agent that has not adhered to a demineralized surface on a tooth.

Following rinsing, the teeth are contacted with the probe compound. In some embodiments, this step entails contacting the teeth or oral cavity with a detector composition that contains the probe compound. This step is advantageously practiced using a dental appliance (wherein the detector composition is disposed therein or thereon). One such example of a dental appliance is a dental tray which may be configured to receive the detector composition and to be brought into contact with at least one tooth. As is known in the art, dental trays may be manufactured from any suitable material, including rubbers and plastics, including polyethylenes, acrylics, polypropylenes, and ethyl vinyl acetates, including metals, including paper and cardboard, and including resins in accordance with conventional methods known in the art. Although the trays may be customized for a user, in other embodiments, they are non-customized but are still relatively pliable in order to appropriately fit over one or more teeth of the user so as to allow the teeth to make an impression in the detector composition, and then be comfortably removed. Accordingly, various design parameters of the dental tray, including type of material, thickness, porosity, and the presence or absence of any other structural features, e.g., a mesh or some other separating means, and size, are well within the skill of the ordinary artisan. Representative examples of dental trays which may be suitable for use in the present invention are described in U.S. Pat. Nos. 2,703,452; 3,654,703; 5,415,544; 8,485,821; 6,749,428; 3,339,547; 3,536,069; and 8,721,332.

The detector composition, which as described hereinabove may be a curable or non-curable dental impression material or a bite registration material or some other orally acceptable pasty composition, is advantageously malleable and possesses other physical properties such that it may be placed onto a dental appliance such as onto (e.g., into a recess or reservoir of) a dental tray, and then placed onto the teeth so that the teeth may make an impression therein, to allow for the colorimetric reaction between the binding agent and the probe compound to occur, and is removable from the teeth intact. As a result of this step, the teeth will make an impression in the detector composition. Typically, contacting the teeth with the detector composition for about a minute or less, e.g., about 10 to about 30 seconds, and in some embodiments from about 10 to about 20 seconds, will suffice for this purpose.

In other embodiments, the dental appliance is dental tape or an occlusal paper or sheet which, when having the detector composition disposed thereon, may be applied to the teeth and affixed thereto for the requisite time for the colorimetric reaction to occur.

More broadly, and as in the case of the binding composition, the detector composition may be applied to the teeth in accordance with any dentally acceptable manner. For example, the detector composition may be applied to the teeth without the use of a dental appliance, such as by aerosol or non-aerosol spray, syringe, rinse, gel, or as a varnish or paste. As persons skilled in the art would appreciate, in these embodiments, the color reaction is observable in the oral cavity, i.e., directly on the tooth.

Figure 2:
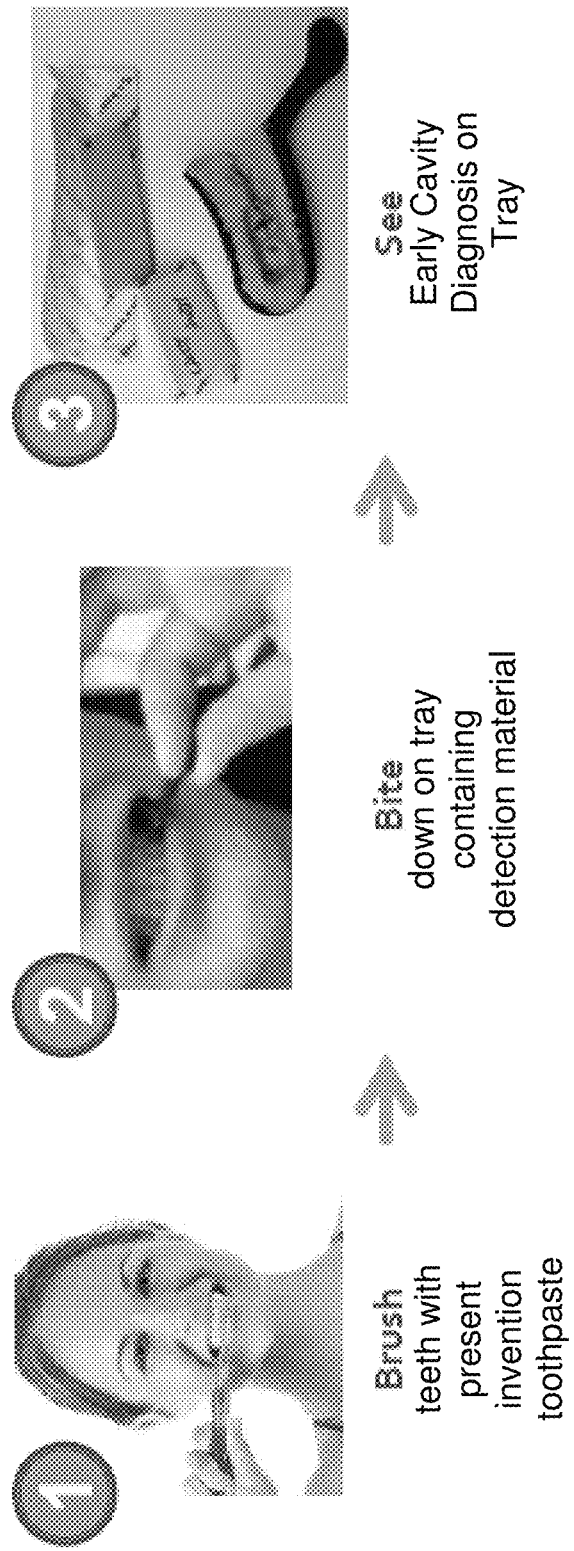
FIG. 2 is a series of photographs showing an embodiment of the present method and the visual detection of the reaction product on a detector composition disposed in a dental tray, thus indicating presence of demineralization.
Figure 3:
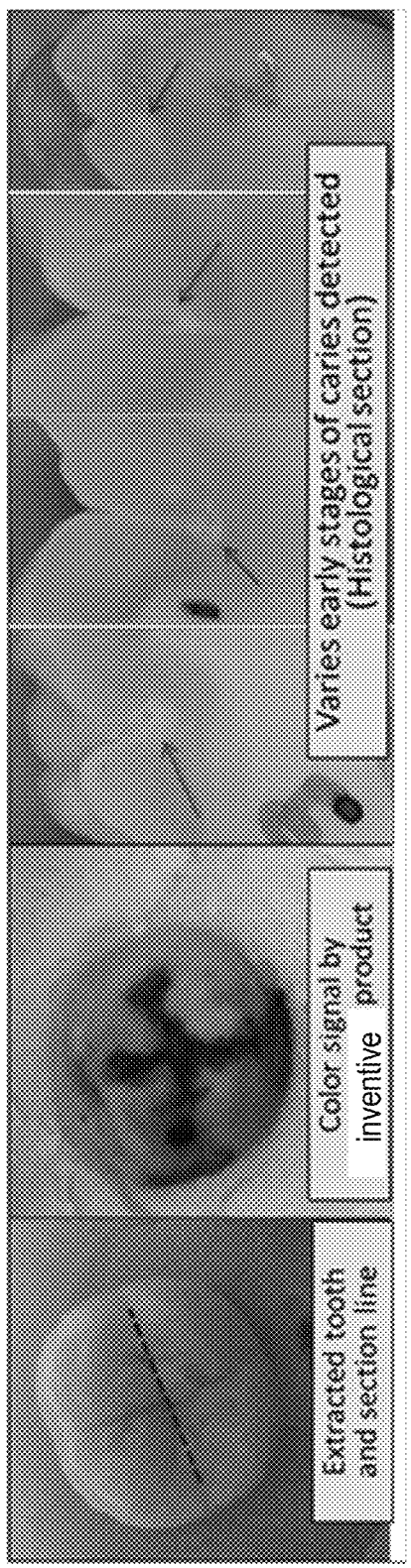
FIG. 3 is a series of photographs showing the colored reaction product on a tooth, and accompanying histological examination confirming early stage of caries.
Figure 4:
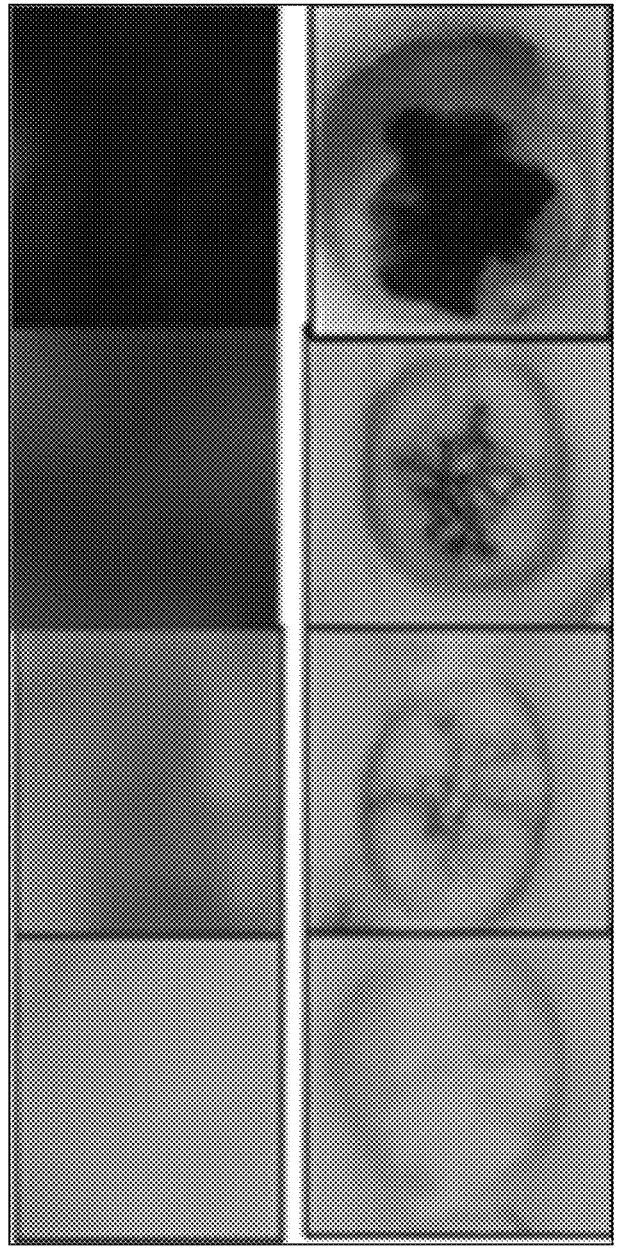
FIG. 4 is a series of photographs that show a correlation between intensity of color of the reaction product with the extent of demineralization.
Figure 5:
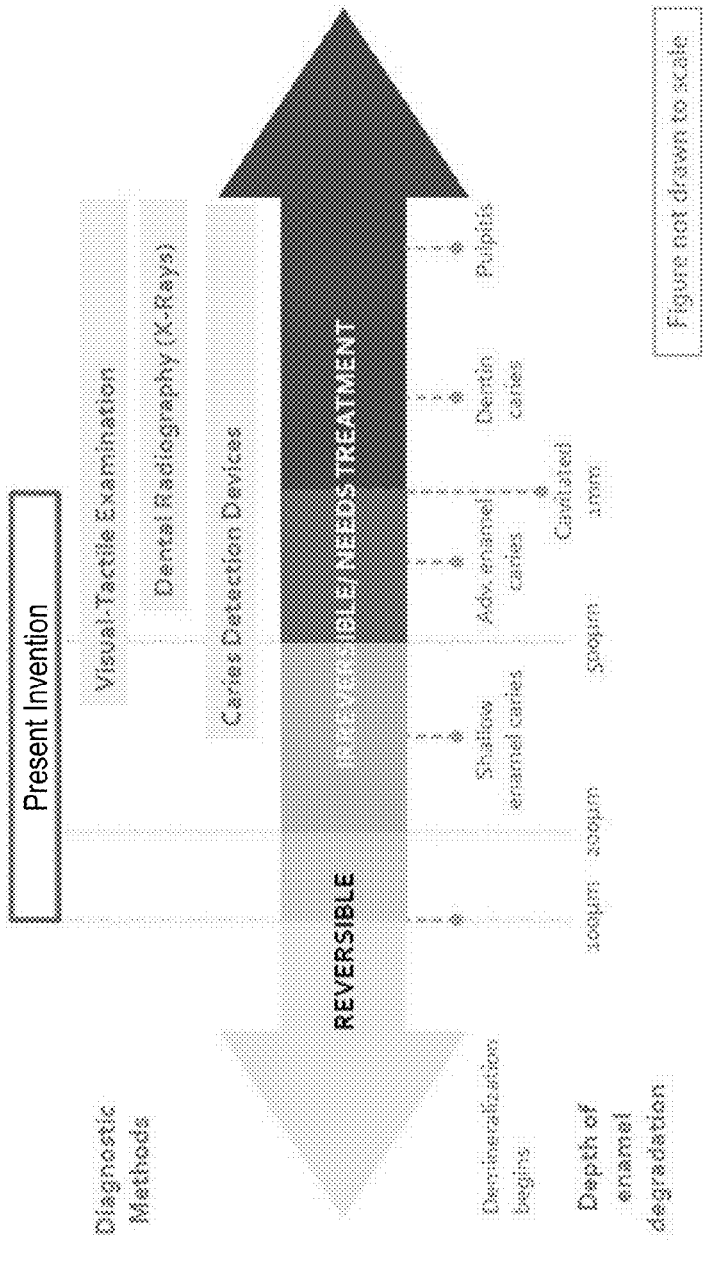
FIG. 5 is a schematic diagram showing the wide spectrum of demineralization that is detectable with the present invention.

The reaction product of the binding agent or compound and probe compound may be visually detected on both the demineralized surface of the tooth as well as on the detector composition. See FIGS. 2 and 3. Thus, the method of the present invention is particularly convenient for the home user in that it does not require an examination or analysis of the teeth themselves. Rather, the presence of demineralization will be visually apparent. Moreover, the extent of demineralization will also be apparent as a function of the intensity of the color (relative to a control, which may be produced by comparison to a histological exam). Thus, in cases where the colorimetric reaction is relatively light, the user is alerted to demineralization that may be reversible in nature (see, FIG. 4). The intensity of the color reaction is greater with the degree of demineralization, in part because more binding agent binds to that surface. FIG. 5 correlates depth of caries with reversibility and irreversibility of demineralization, and shows the wide spectrum of diagnostic and therapeutic efficacy of the present invention. Thus, in the case of a light color reaction, the user may take assertive steps to remineralize the teeth, by applying thereto and preferably on a regular basis, an orally acceptable composition containing a remineralizing agent.

Representative examples of remineralizing agents that may be suitable for use in the present invention are well known in the art and include fluorides (as disclosed hereinabove) such as sodium fluoride and stannous fluoride, typically in concentrations of about 0.25% w/v to about 5.0% w/v. Of course, in some embodiments, and regardless of whether a separate remineralization step is conducted after application of the binding and detector compositions (and analyzing the results), the remineralization agent may be present in the binding composition, the detector composition or both.

In other cases, the extent of the colorimetric reaction may be relatively strong, i.e., a darker color shows on the detector composition, in which case the user is alerted to what may well be an irreversible stage of demineralization, in which case professional dental intervention would be prudent. See FIGS. 4 and 5.

In addition to the foregoing, the user may capture a photograph of the results, e.g., that are on a dental appliance, simply by using a mobile phone camera. The photograph from each use of the present invention can be stored and analyzed by the user or a medical professional, e.g., compared to results obtained in subsequent tests as a way of self-monitoring the extent of remineralization or, on the other hand, the extent of even further demineralization.

The site of demineralization may be present on various areas of the tooth, including the enamel, dentin, and cementum. These types of demineralized surfaces include caries, cracks, fractures, etc.

Packages and Kits

The individual compositions that may be used in the practice of the present invention, e.g., the binding composition and the detector composition, may be prepared and/or purchased separately. Alternatively, they may be disposed separate containers and packaged together in the form of a unitary kit, which may be made of plastic or any other disposable (and preferably recyclable) substance(s). The containers in which the respective compositions may be disposed are also well known in the art, and include, for example, jars, cups, cans, tubes, aerosol cans, syringes, tubs, pumps, bottles, and other liquid and semi-solid or colloidal holding or dispensing means. One or more of the materials used to make the package or kit, or containers therein, may be biodegradable, which as used herein, refers to a material capable of being broken down especially into innocuous products by the action of living things (such as microorganisms).

In some embodiments of the present invention, the binding agent or compound may be provided apart from the carrier, and in its own separate container. In these embodiments, the binding agent or compound may be dispensed from its container (which may be any appropriate container that could hold and dispense a solid, e.g., powdery substance, liquid, or gel) and mixed with the carrier, e.g., a dentifrice, suitably prior to use. In yet other embodiments, the package or kit may include a container having disposed therein the binding agent or compound, e.g., in solid, powdery form, but which does not include the carrier, e.g., the dentifrice. In these embodiments, the carrier may be obtained separately. Likewise, in yet other embodiments, the package or kit may include a container having disposed therein the probe compound, e.g., in solid, powdery form, but which does not include the carrier, e.g., the dental impression material, the bite registration material or the flour/gum/clay mixture. In these embodiments, the carrier composition may be obtained separately. Thus, the kit may contain one or more separate containers having disposed therein, a) the binding agent/compound, b) the carrier composition for the binding agent/compound, c) the carrier composition containing the binding agent/compound, d) the probe compound, e) the carrier composition for the probe compound, and f) the carrier composition containing the probe compound. In some embodiments, kits designed for home use may contain c) and f), or c), e) and f). In some embodiments, kits designed for professional use may contain a) and d).

In addition to the above-described compositions, the packages or kits of the present invention may include printed instructions for their use, which may include i) contacting the tooth or oral cavity of a subject with the orally acceptable, binding composition; ii) removing unbound binding compound; iii) contacting the tooth or the oral cavity with the orally acceptable, detector composition; and iv) detecting formation of the complex between the binding compound and the probe compound as an indication of the presence of demineralization on the surface of the tooth. The printed information may also include a colorimetric index, that correlates extent of the color reaction with the degree of demineralization that would be specific to a particular binding agent/probe compound combination.

The packages or kits of the present invention may also include an applicator for the binding composition, e.g., a toothbrush.

In other embodiments, the packages or kits of the present invention may include a dental appliance as disclosed herein, such as dental tape, occlusal paper or sheets, or one or more dental trays, each having a shell, reservoir, or recess adapted to receive an amount of the detector composition and to receive one or more teeth, for purposes of making an impression, or a syringe.

In some other embodiments, the package or kit may include a syringe for applying the binding composition and/or the detector composition to the teeth. Examples of syringes include the ULTRA-ETCH Empty Syringe and MONOJECT 3 cc Syringe with Luer Tip.

In yet other embodiments, the packages or kits of the present invention may include a separate container containing an orally acceptable composition containing a remineralizing agent.

In yet other embodiments, the packages or kits of the present invention may include a separate container containing an orally acceptable composition containing a rinsing agent.

The invention will now be described in terms of the following, non-limiting example.

EXAMPLE

The following ex vivo study involved comparing an embodiment of the present invention, using Fe (III)-pyrophosphate and propyl gallate as the binding compound and the detector compound, respectively, with other known caries detection modalities. The results of the study demonstrate that the present invention exhibited superior sensitivity, specificity, PPV (positive predictive value) and NPV (negative predictive value) values than any of the known detection modalities, as compared to histologic analysis which was used as the gold standard control.

The comparative study utilized 16 sets of quadrant teeth models, containing a total of 72 extracted teeth. In all, 94 occlusal areas of the teeth were examined.

The known caries detection modalities that were used for purposes of the comparisons included a clinical exam conducted by three different dentists, in accordance with protocols known in the art (e.g., Guerrieri, et al. Br. Dent. J. 213 (11):551-7 (2012) ("Initial Clinical Examination" in page 552)), the KaVo Diagnodent (Theocharopoulou, et al. Eur. J. Paed. Dent. 16(1):51-5 (2015)), and the Midwest Caries ID (Van Hilsen, et al., BMC Oral Health 13:16 (2013)).

The inventive embodiment entailed measuring the magnitude of the colorimetric reaction on the dental tray that was used to deliver the detector composition to the teeth treated with the binding composition, which was measured by Olympus Crystaleye®, which is known in the art as a dental spectrophotometer. The magnitude of the color difference (i.e., measured as dE values) was compared to the depth of caries lesions as confirmed by the histological analysis, with a Peason's correlation R of 0.93. The binding composition contained Fe (III)-pyrophosphate formulated in a toothpaste and the detector composition contained about 2.4% w/v propyl gallate formulated in a carrier containing about 55.9% w/v of flour and 29.4% w/v of a gum, about 2.9% w/v bentonite clay, and about 0.25% w/v sodium fluoride.

Results are shown in Table 1.

TABLE 1

Accuracy of Present Invention product in ex-vivo study

|  | Dentist | KaVo Diagnodent | Midwest Caries ID | Present Invention |
| --- | --- | --- | --- | --- |
| Sensitivity | 18% | 27% | 77% | 82% |
| Specificity | 90% | 71% | 11% | 86% |
| PPV | 82% | 69% | 67% | 93% |
| NPV | 32% | 29% | 17% | 67% |

The data show that the embodiment of the present invention was superior to the known caries detection modalities. Detection performance is usually measured as the sum of a method's sensitivity and specificity.

Figure 6:
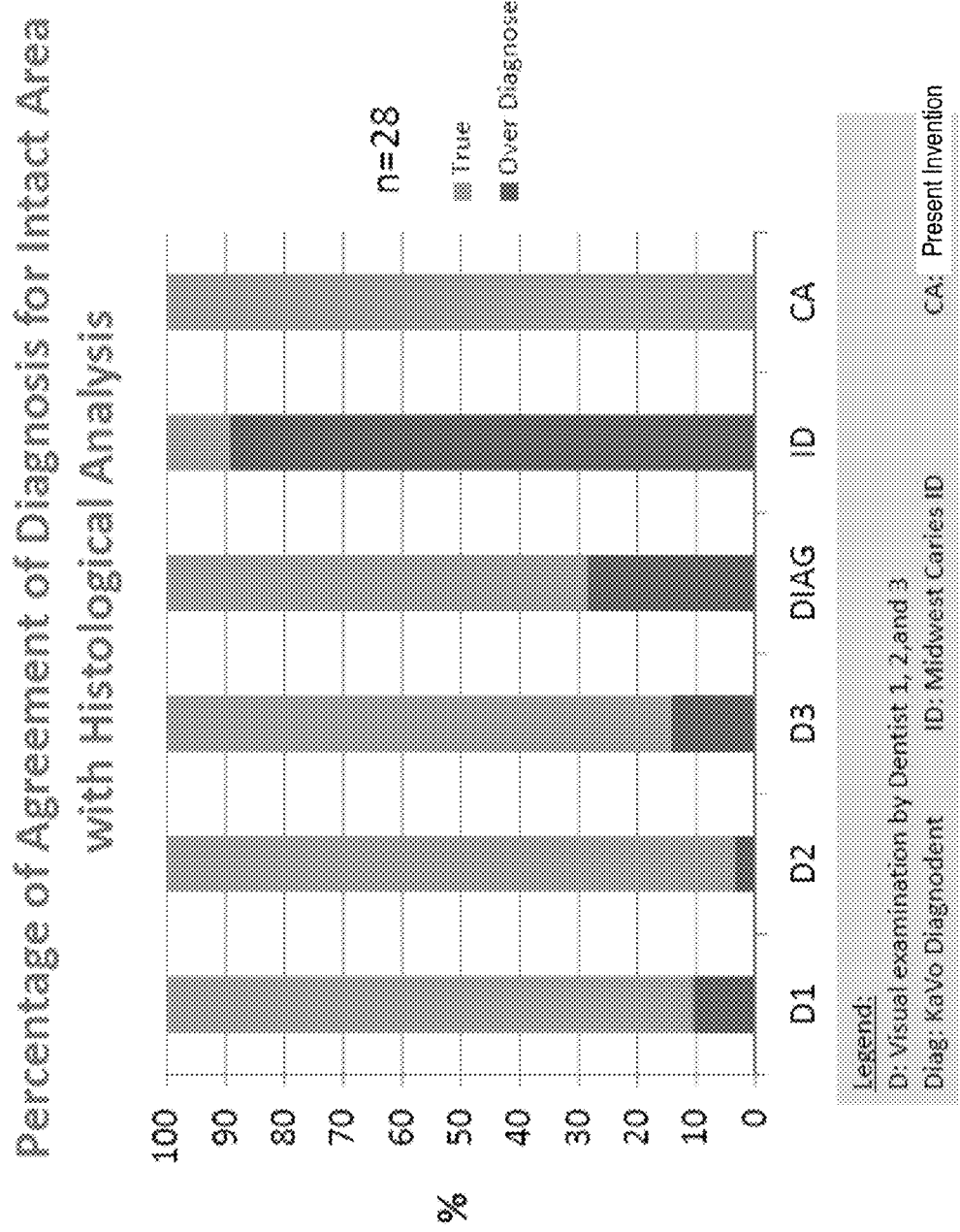
FIG. 6 is a bar graph showing data that demonstrates the superiority of the present invention compared to several clinical caries detection modalities, from the standpoint of false positive results.
Figure 7:
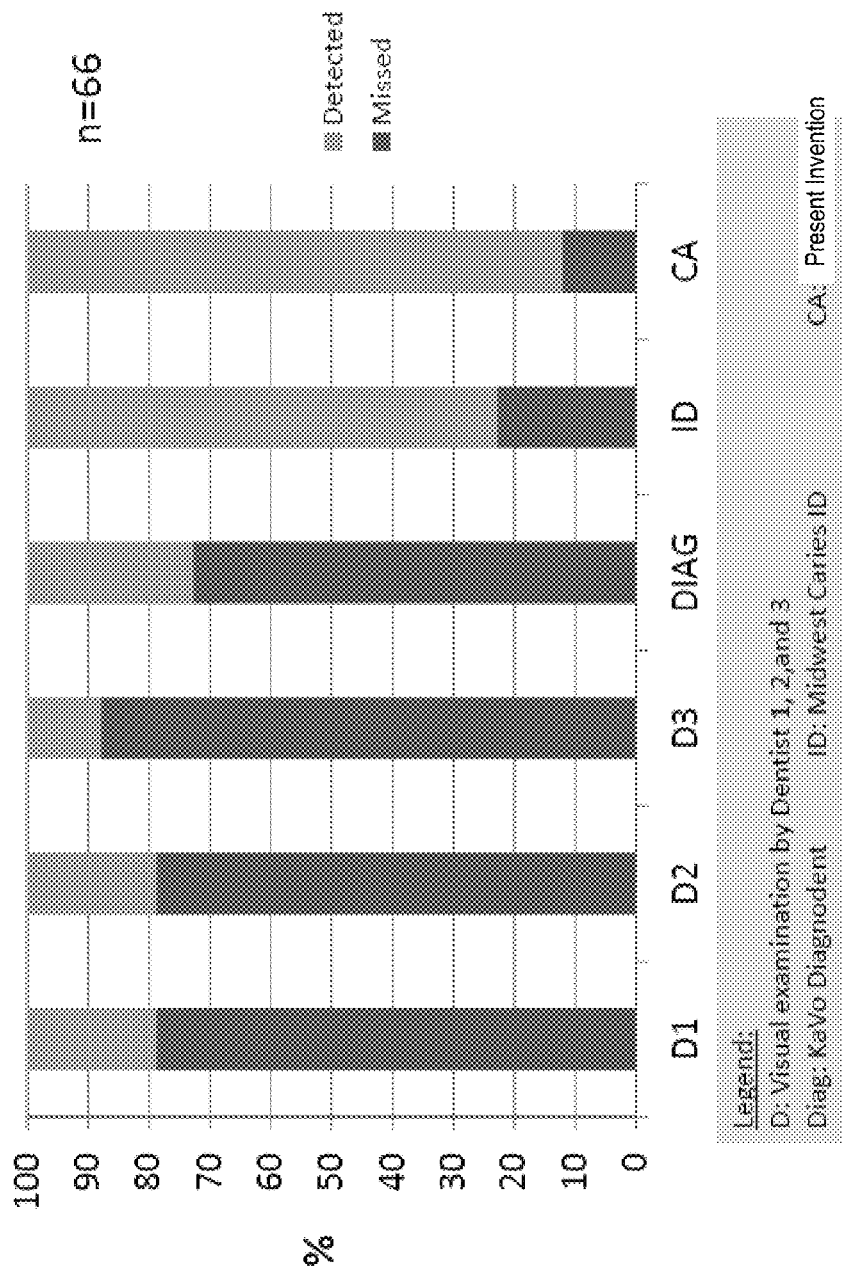
FIG. 7 is a bar graph showing data that demonstrates the superiority of the present invention compared to several clinical caries detection modalities, from the standpoint of false negative results.

Further data generated from the comparative study are shown in FIGS. 6 and 7. FIG. 6 is a bar graph that compares the present invention against each of the known caries detection modalities from the standpoint of overdiagnosed caries, i.e., false positive results. The data show that in the sample size study, the present invention was 100% accurate from this standpoint, and in rather stark contrast to KaVo Diagnodent and especially Midwest Caries ID (and to a lesser extent the visual examinations by the three dentists). FIG. 7 is also a bar graph and compares the present invention to the comparative methods from the standpoint of missed diagnosis of caries, i.e., false negative results. Here again, the present invention was about twice as accurate in this respect as compared to the closest comparative caries detection modality, Midwest Caries ID (at about 22% false negative results). The percentages of false negative results obtained by each of the three dentists and via KaVo Diagnodent were all substantially (i.e., about seven-fold) higher than the present invention.

All patent publications and non-patent publications are indicative of the level of skill of those skilled in the art to which this invention pertains. All these publications are herein incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A kit for detecting demineralization of a surface of a tooth, comprising a) a first container comprising an orally acceptable, binding composition comprising iron (III) pyrophosphate (Fe(III)-PP); and b) a second container comprising an orally acceptable, detector composition comprising gallic acid or an ester thereof that reacts with the Fe(III)-PP to form a visually detectable reaction product.

2. The kit of claim 1, wherein the binding composition, the detector composition or both, is selected from the group consisting of pastes, varnishes, dentifrices, gels, creams, chewing gum, tablets, candies, capsules, mints, sprays, mouthwashes, rinses, whitening systems, powders, rinses, and foams.

3. The kit of claim 2, wherein the dentifrice is toothpaste.

4. The kit of claim 3, wherein the Fe(III)-PP is present in the toothpaste in an amount of from about 0.075% to about 7.5% w/v, and wherein the gallic acid or orally acceptable ester thereof is present in the detector composition in an amount of from about 0.5% to about 10% w/v.

5. The kit of claim 1, wherein the detector composition further comprises a dental impression material or a bite registration material.

6. The kit of claim 1, wherein the detector composition further comprises a gum and flour.

7. The kit of claim 6, wherein the detector composition further comprises a hydrophilic clay.

8. The kit of claim 7, wherein the clay is sodium bentonite.

9. The kit of claim 7, wherein the flour is present in an amount of from about 40% to about 70% w/v, the gum is present in an amount of from about 15% to about 40% w/v, and the clay is present in an amount of from about 1% to about 10% w/v.

10. The kit of claim 9, wherein the detector composition further comprises an oil, a water-miscible solvent, an enhancing agent, an active dental agent, or a combination of two or more thereof.

11. The kit of claim 10, wherein the enhancing agent or the active dental agent comprises a fluoride.

12. The kit of claim 1, wherein the binding composition, the detector composition or both the binding composition and the detector composition further comprise a flavoring agent, a coloring agent, a buffering agent, a sensate ingredient, or a combination of two or more thereof.

13. The kit of claim 1, further comprising c) a dental appliance.

14. The kit of claim 13, wherein the dental appliance is a dental tray.

15. The kit of claim 1, wherein the detector composition comprises propyl gallate.

16. The kit of claim 1, further comprising printed instructions for i) contacting the tooth of a subject with the orally acceptable binding composition; ii) removing unbound Fe(III)-PP; iii) contacting the tooth with the orally acceptable, detector composition; and iv) detecting formation of the reaction product as an indication of the presence or extent of demineralization on the surface of the tooth.

17. A method for detecting demineralization of a surface of a tooth, comprising a) contacting the tooth of a subject with an orally acceptable binding composition comprising iron (III) pyrophosphate (Fe(III)-PP) that binds to a demineralized surface of the tooth; b) removing unbound Fe(III)-PP; c) contacting the tooth with an orally acceptable detector composition comprising gallic acid or an ester thereof that reacts with Fe(III)-PP to form a visually detectable reaction product; and d) detecting formation of the reaction product as an indication of the presence or extent of surface demineralization of the tooth.

18. The method of claim 17, wherein the binding composition is brought into contact with the tooth in a form selected from the group consisting of pastes, varnishes, dentifrices, gels, creams, gum, tablets, candies, capsules, mints, sprays, mouthwashes, whitening systems, powders, rinses, and foams.

19. The method of claim 18, wherein the dentifrice is toothpaste.

20. The method of claim 19, wherein the Fe(III)-PP is present in the toothpaste in an amount of from about 0.075% to about 7.5% w/v, and wherein the wherein the gallic acid or orally acceptable ester thereof is present in the detector composition in an amount of from about 0.5% to about 10% w/v.

21. The method of claim 17, wherein the detector composition is brought into contact with the tooth in a form of a dental impression material or a bite registration material.

22. The method of claim 17, wherein the detector composition further comprises flour which is present in an amount of from about 40% w/v to about 70% w/v, a gum which is present in an amount of from about 15% w/v to about 40% w/v, and a hydrophilic clay which is present in an amount of from about 1% w/v to about 10% w/v.

23. The method of claim 22, wherein the gallic acid or ester thereof is present in an amount of from about 0.5% w/v to about 10% w/v.

24. The method of claim 22, wherein the detector composition further comprises an oil, a water-miscible solvent, an enhancing agent, a chelating agent, an active dental agent or a combination of two or more thereof.

25. The method of claim 17, wherein c) comprises contacting the tooth with the detector composition which is disposed on a dental appliance configured to receive the detector composition and to be brought into contact with at least one tooth such that an impression of the at least one tooth is made in the detector composition, and wherein said method further comprises c1) removing the dental appliance from the tooth, and wherein d) comprises detecting the reaction product on the detector composition.

26. The method of claim 25, wherein the dental appliance is a dental tray.

27. The method of claim 17, wherein d) comprises detecting the reaction product on the tooth.

28. The method of claim 17, wherein the probe compound is propyl gallate.

* * * * *